(12) United States Patent
Asada et al.

(10) Patent No.: US 6,281,231 B1
(45) Date of Patent: Aug. 28, 2001

(54) 2,6-DICHLORO-4-PYRIDINEMETHANOL DERIVATIVES AND AGRICULTURAL CHEMICALS

(75) Inventors: Toru Asada, Inba-gun; Mika Iiyama, Sakura; Hiroyuki Tsuboi, Yachiyo; Takashi Gotou, Sakura, all of (JP)

(73) Assignee: Dainippon Ink and Chemical, Inc., Tokyo (JP)

( * ) Notice: Subject to any disclaimer, the term of this patent is extended or adjusted under 35 U.S.C. 154(b) by 0 days.

(21) Appl. No.: 09/508,261

(22) PCT Filed: Sep. 9, 1998

(86) PCT No.: PCT/JP98/04036

§ 371 Date: Mar. 9, 2000

§ 102(e) Date: Mar. 9, 2000

(87) PCT Pub. No.: WO99/12907

PCT Pub. Date: Mar. 18, 1999

(30) Foreign Application Priority Data

Sep. 10, 1997 (JP) .................................................. 9-245279
Sep. 19, 1997 (JP) .................................................. 9-245280

(51) Int. Cl.⁷ ......................... C07D 213/02; A61K 31/44
(52) U.S. Cl. ........................ 514/332; 546/255; 546/339; 546/340; 546/344; 514/277
(58) Field of Search .................................. 546/340, 344, 546/255, 339; 514/277, 332

(56) References Cited

U.S. PATENT DOCUMENTS

| | | | |
|---|---|---|---|
| 4,063,926 | 12/1977 | Tomlin et al. | 71/94 |
| 4,851,396 | 7/1989 | Lambert et al. | 514/63 |

FOREIGN PATENT DOCUMENTS

| | | | |
|---|---|---|---|
| 195 45 637 | 6/1997 | (DE) . | |
| 244728 | * 4/1987 | (EP) | 546/514 |
| 0 246 171 | 11/1987 | (EP) . | |
| 0 268 775 | 6/1988 | (EP) . | |
| 0 334 813 A2 | 9/1989 | (EP) . | |
| 62-277361 | 12/1987 | (JP) . | |
| WO 96 37472 | 11/1986 | (WO) . | |
| WO 97/20770 | 6/1997 | (WO) . | |
| WO 97/20840 | 6/1997 | (WO) . | |
| WO 99 58502 | 11/1999 | (WO) . | |

* cited by examiner

Primary Examiner—Zinna Northington Davis
(74) Attorney, Agent, or Firm—Armstrong, Westerman, Hattori, McLeland & Naughton, LLP

(57) ABSTRACT

The object is to provide a novel compound, with which there is little possibility of phytotoxicity for crop plants, and which is greatly effective in controlling various plant diseases caused by viruses pathogenic to plants, by bacteria, and by molds, and to provide agricultural chemicals, particularly agents for controlling plant diseases, containing this compound, 2,6-dichloro-4-pyridinemethanol, and/or a benzoic acid ester thereof as an active ingredient. As means for achieving the object, 2,6-dichloro-4-pyridinemethanol derivatives, 2,6-dichloro-4-pyridinemethanol, benzoic acid esters thereof, and agricultural chemicals containing these compounds as active ingredients are provided, the 2,6-dichloro-4-pyridinemethanol derivative being expressed by general formula (1):

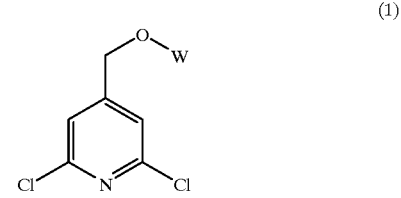

(1)

wherein W denotes an optionally substituted $C_1$ to $C_8$ alkyl group, a trifluoromethylpyridyl group, $-COR^1$, $-SO_2R^2$, $-PO(OR^3)_2$, $-CONHR^4$, $-COOR^4$, $-COCOR^4$, or $-SiR^5R^6R^7$, in which: $R^1$ denotes an optionally substituted $C_1$ to $C_{18}$ alkyl group, an optionally substituted $C_1$ to $C_{18}$ alkenyl group, a phenyl group which has one or more specific substituent groups, or a 5- or 6-membered heterocyclic ring residue which has any one of a nitrogen atom, an oxygen atom, or a sulfur atom as a ring component atom; $R^2$ denotes an alkyl group or a phenyl group; $R^3$ denotes an alkyl group; $R^4$ denotes an alkyl group or a phenyl group; and each of $R^5$ to $R^7$ denotes an alkyl group.

12 Claims, No Drawings

2,6-DICHLORO-4-PYRIDINEMETHANOL DERIVATIVES AND AGRICULTURAL CHEMICALS

TECHNICAL FIELD

The present invention relates to a novel 2,6-dichloro-4-pyridinemethanol derivative and agricultural chemicals, particularly agents for controlling plant diseases, containing this compound as an active ingredient.

BACKGROUND ART

In agricultural production, there are needs for controlling various fungi pathogenic to plants, pests, weeds, and the like, and agricultural chemicals have hitherto been useful means therefor. However, there have been problems in that some compounds are phytotoxic for plants, and particularly for the crop plants to which the agricultural chemicals are applied, even though these compounds have excellent activity as agricultural chemicals, or in that even compounds which are not phytotoxic are not effective enough for practical use. Accordingly, production of compounds which are greatly effective as agricultural chemicals and which have little phytotoxicity has always been demanded.

Japanese Patent No. 2514823 and Japanese Patent Application, First Publication (Kokai), No. 1-283270, disclose that 2,6-dichloroisonicotinic acid derivatives having specific structures are active in protecting crop plants from pathogenic microorganisms. However, these compounds are phytotoxic for some types of crops, although these compounds were effective.

On the other hand, 2,6-dichloro-4-pyridinemethanol, to which the present invention relates, can be synthesized, for example, by bringing about a reduction reaction using 2,6-dichloroisonicotinic acid or an ester thereof as a starting material. (J. Prakt. Chem., Vol. 134, pp. 177–187 (1932); West German Patent Publication No. 3,615,293) However, neither a 2,6-dichloro-4-pyridinemethanol derivative according to the present invention nor use of 2,6-dichloro-4-pyridinemethanol and a 2,6-dichloro-4-pyridinemethanol derivative as an agricultural chemical has been known.

The object to be achieved by the present invention is to provide a novel compound with which there is little possibility of phytotoxicity for crop plants, and which is greatly effective in controlling various plant diseases caused by viruses pathogenic to plants, by bacteria, and by molds, and to provide agricultural chemicals, particularly agents for controlling plant diseases, containing this compound, i.e., 2,6-dichloro-4-pyridinemethanol, and/or a benzoic acid ester thereof as an active ingredient.

DISCLOSURE OF INVENTION

As a result of investigations in order to achieve the above object, the present inventors have arrived at the present invention, finding that a 2,6-dichloro-4-pyridinemethanol derivative which is expressed by general formula (1) is effective as an agricultural chemical, and particularly for controlling plant diseases, with a small amount used, and that there is no possibility of the compound being phytotoxic for plants.

That is to say, the present invention includes:
(a) a 2,6-dichloro-4-pyridinemethanol derivative expressed by the following general formula (1):

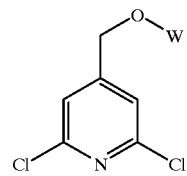

wherein W denotes: a $C_1$ to $C_8$ alkyl group which is unsubstituted or which is optionally substituted with an alkoxy group, an alkylthio group, a cyano group, a phenyl group, or a pyridyl group, the pyridyl group being optionally substituted with a halogen atom; a trifluoromethylpyridyl group; —$COR^1$; —$SO_2R^2$; —$PO(OR^3)_2$; —$CONHR^4$; —$COOR^4$; —$COCOR^4$; or —$SiR^5R^6R^7$;

$R^1$ denotes:
a $C_1$ to $C_{18}$ alkyl group which is unsubstituted or which is optionally substituted with an alkoxy group, an alkylthio group, a phenyl group, a hydroxy group, a phenylalkoxy group, a phenylalkylthio group, an alkyloxycarbonyl group, an alkylcarbonylamino group, or a phenoxy group, the phenyl group being optionally substituted with an alkoxy group;
a $C_1$ to $C_{18}$ alkenyl group which is optionally substituted with a phenyl group, the phenyl group being optionally substituted with an alkoxy group;
a phenyl group which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group; or
a 5- or 6-membered heterocyclic ring residue which has any one of a nitrogen atom, an oxygen atom, or a sulfur atom as a ring component atom, the heterocyclic ring residue being optionally substituted with a $C_1$ to $C_4$ alkyl group;

$R^2$ denotes a $C_1$ to $C_{12}$ alkyl group or a phenyl group which is optionally substituted with a $C_1$ to $C_{12}$ alkyl group;

$R^3$ denotes a $C_1$ to $C_4$ alkyl group;

$R^4$ denotes a $C_1$ to $C_3$ alkyl group or a phenyl group; and each of $R^5$ to $R^7$, being the same or different, denotes a $C_1$ to $C_4$ alkyl group;

(b) a 2,6-dichloro-4-pyridinemethanol derivative as described in (a), wherein W in general formula (1) denotes a $C_1$ to $C_8$ alkyl group or a trifluoromethylpyridyl group, the C to $C_8$ alkyl group being unsubstituted or being optionally substituted with an alkoxy group, an alkylthio group, a cyano group, a phenyl group, or a pyridyl group, the pyridyl group being optionally substituted with a halogen atom;

(c) a 2,6-dichloro-4-pyridinemethanol derivative as described in (a), wherein W in general formula (1) denotes —$COR^1$ in which $R^1$ denotes:
a $C_1$ to $C_{18}$ alkyl group which is unsubstituted or which is substituted with an alkoxy group, an alkylthio group, a phenyl group, a hydroxy group, a phenylalkoxy group, a phenylalkylthio group, an alkyloxycarbonyl group, an alkylcarbonylamino group, or a phenoxy group, the phenyl group being optionally substituted with an alkoxy group;

a $C_1$ to $C_{18}$ alkenyl group which is unsubstituted or which is substituted with a phenyl group which is optionally substituted with an alkoxy group;

a phenyl group which has one or more substituent groups, being the same or different, the substituent groups being selected from: halogen atoms; $C_1$ to $C_6$ alkyl groups which are optionally substituted with a halogen atom, $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group; or a 5- or 6-membered heterocyclic ring residue which has any one of a nitrogen atom, an oxygen atom, or a sulfur atom as a ring component atom, the heterocyclic ring residue being optionally substituted with a $C_1$ to $C_4$ alkyl group;

(d) a 2,6-dichloro-4-pyridinemethanol derivative as described in (c), wherein W in general formula (1) denotes —COR$^1$ in which R$^1$ denotes an alkenyl group which is unsubstituted or which is substituted with a phenyl group which is optionally substituted with an alkoxy group;

(e) a 2,6-dichloro-4-pyridinemethanol derivative as described in (c), wherein W in general formula (1) denotes —COR$^1$ in which R$^1$ denotes a phenyl group which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group;

(f) a 2,6-dichloro-4-pyridinemethanol derivative as described in (e), wherein W in general formula (1) denotes —COR$^1$ in which R$^1$ denotes a $C_1$ to $C_{12}$ alkoxyphenyl group which is optionally substituted with a halogen atom;

(g) a 2,6-dichloro-4-pyridinemethanol derivative as described in (a), wherein W in general formula (1) denotes —SO$_2$R$^2$ in which R$^2$ denotes a $C_1$ to $C_{12}$ alkyl group or a phenyl group which is optionally substituted with a $C_1$ to $C_{12}$ alkyl group;

(h) a 2,6-dichloro-4-pyridinemethanol derivative as described in (a), wherein W in general formula (1) denotes —PO(OR$^3$)$_2$ in which R$^3$ denotes a $C_1$ to $C_4$ alkyl group;

(i) a 2,6-dichloro-4-pyridinemethanol derivative as described in (a), wherein W in general formula (1) denotes —CONHR$^4$, —COOR$^4$, or —COCOR$^4$ in which R$^4$ denotes a $C_1$ to $C_3$ alkyl group or a phenyl group;

(j) a 2,6-dichloro-4-pyridinemethanol derivative as described in (a), wherein W in general formula (1) denotes —SiR$^5$R$^6$R$^7$ in which each of R$^5$ to R$^7$, being the same or different, denotes a $C_1$ to $C_4$ alkyl group;

(k) an agricultural chemical comprising as an active ingredient at least one 2,6-dichloro-4-pyridinemethanol derivative as described in any one of (a) to (j);

(1) an agricultural chemical comprising as an active ingredient 2,6-dichloro-4-pyridinemethanol, which is expressed by general formula (1) in which W denotes a hydrogen atom, and/or benzoic acid ester of 2,6-dichloro-4-pyridinemethanol, which is expressed by general formula (1) in which W denotes a phenylcarbonyl group;

general formula (1):

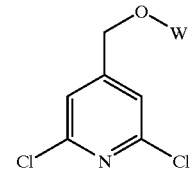

(1)

(m) an agricultural chemical as described in (k) or (l), wherein the agricultural chemical is an agent for controlling a plant disease; and (n) an agricultural chemical as described in (m), wherein the agent for controlling a plant disease is an agent for controlling rice blast.

BEST MODE FOR CARRYING OUT THE INVENTION

In the compound of the present invention, expressed by general formula (1):

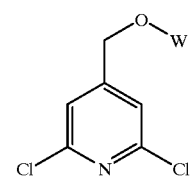

(1)

an alkyl group denoted by W and R$^1$ to R$^7$, substituted or unsubstituted, having a predetermined number of carbons, is selected from straight, branched, and cyclic alkyl groups such as methyl, ethyl, n-propyl, isopropyl, n-butyl, isobutyl, 2-butyl, tert-butyl, n-pentyl, n-hexyl, n-octyl, 2-ethylhexyl, n-dodecyl, n-octadecyl, n-eicosyl, cyclopropyl, cyclopentyl, cyclohexyl, methoxymethyl, methoxyethyl, butoxybutyl, methoxypentyl, dodecyloxyethyl, ethylthioethyl, methylthiopropyl, methylthiobutyl, octylthiopropyl, cyanoethyl, cyanopropyl, cyanohexyl, benzyl, phenylethyl, phenylpropyl, ethoxybenzyl, methoxyphenylpropyl, pyridylmethyl, chloropyridylmethyl, hydroxymethyl, hydroxyhexyl, benzyloxymethyl, benzylthioethyl, methoxycarbonylbutyl, acetylaminomethyl, and phenoxyethyl.

Examples of an alkenyl group, denoted by R$^1$, which is optionally substituted with a phenyl group, the phenyl group being optionally substituted with an alkoxy group, are ethenyl, propenyl, butenyl, pentenyl, hexenyl, heptadecenyl, butadienyl, pentadienyl, heptadecadienyl, phenylethenyl, phenylpropenyl, and methoxyphenylethenyl.

Examples of a phenyl group, denoted by R$^1$, which has one or more predetermined substituent groups, being the same or different, are fluorophenyl, chlorophenyl, bromophenyl, methylphenyl, hexylphenyl, trifluoromethylphenyl, chloromethylphenyl, methoxyphenyl, hexyloxyphenyl, dodecyloxyphenyl, cyclohexyloxyphenyl, difluoromethoxyphenyl, trifluoroethoxyphenyl, propenyloxyphenyl, nitrophenyl, aminophenyl, N,N40-dimethylaminophenyl, cyanophenyl, acetylaminophenyl, benzoylaminophenyl, acetyloxyphenyl, biphenyl, and phenoxyphenyl.

Examples of a 5- or 6-membered heterocyclic ring residue, denoted by R$^1$, which has any one of a nitrogen atom, an oxygen atom, or a sulfur atom as a ring component atom, the heterocyclic ring residue being optionally substituted with a $C_1$ to $C_4$ alkyl group, are furyl, thienyl, pyrrolyl, pyranyl, pyridinyl, and methylpyridyl.

Examples of a phenyl group, denoted by $R^2$, which is optionally substituted with a $C_1$ to $C_{12}$ alkyl group, are methylphenyl, hexylphenyl, and dodecylphenyl.

Concrete structures of compounds expressed by general formula (1) are exemplified in Tables 1 to 10. It should be noted that 2,6-dichloro-4-pyridinemethanol in Table 1 and benzoic acid ester of 2,6-dichloro-4-pyridinemethanol in Table 5 are known compounds, and the other compounds are novel compounds.

TABLE 1

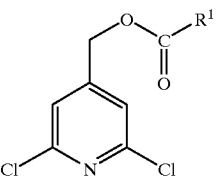

| W |
|---|
| —H |
| —$CH_3$ |
| —$C_2H_5$ |
| —$(CH_2)_2CH_3$ |
| —$CH(CH_3)_2$ |
| —$(CH_2)_3CH_3$ |
| —$CH_2CH(CH_3)_2$ |
| —$CH(CH_3)CH_2CH_3$ |
| —$C(CH_3)_3$ |
| —$(CH_2)_4CH_3$ |
| —$(CH_2)_5CH_3$ |
| —$CH_2CH(C_2H_5)(CH_2)_3CH_3$ |
| —$CH_2OCH_3$ |
| —$C_2H_4OCH_3$ |
| —$C_2H_4SCH_3$ |
| —$C_2H_4OC_2H_5$ |
| —$C_2H_4SC_2H_5$ |
| —$CH_2CN$ |
| —$C_2H_4CN$ |
| —$(CH_2)_3CN$ |
| —$CH_2$—C$_6H_5$ |
| —$(CH_2)_2$—C$_6H_5$ |
| —$CH_2$—(4-pyridyl) |
| —$CH_2$—(3-pyridyl) |
| —$CH_2$—(2-pyridyl) |

TABLE 1-continued

| W |
|---|
| (2,6-dichloro-4-pyridyl)-$CH_2$— |
| 6-chloro-5-trifluoromethylpyridyl-$CH_2$— |

TABLE 2

| $R^1$ |
|---|
| —$CH_3$ |
| —$C_2H_5$ |
| —$(CH_2)_2CH_3$ |
| —$CH(CH_3)_2$ |
| —$(CH_2)_3CH_3$ |
| —$CH_2CH(CH_3)_2$ |
| —$CH(CH_3)CH_2CH_3$ |
| —$C(CH_3)_3$ |
| —$(CH_2)_4CH_3$ |
| —$(CH_2)_5CH_3$ |
| —$(CH_2)_7CH_3$ |
| —$(CH_2)_9CH_3$ |
| —$(CH_2)_{11}CH_3$ |
| —$(CH_2)_{13}CH_3$ |
| —$(CH_2)_{16}CH_3$ |
| —$(CH_2)_{17}CH_3$ |
| —CH=$CH_2$ |
| —CH=$CHCH_3$ |
| —$CH_2$CH=$CH_2$ |
| —CH=CH—CH=$CH_2$ |
| —CH=CH—CH=CH—$CH_3$ |
| —$(CH_2)_7$CH=CH$(CH_2)_7CH_3$ |
| —$(CH_2)_7$CH=CHCH$_2$CH=CH—$(CH_2)_4CH_3$ |
| —$CH_2OCH_3$ |
| —$CH_2OC_2H_5$ |
| —$CH_2O(CH_2)_3CH_3$ |
| —$C_2H_4SC_2H_5$ |
| —$(CH_2)_3OC_2H_5$ |
| —$(CH_2)_4SCH_3$ |
| —$C_2H_4O(CH_2)_3CH_3$ |
| —$C_2H_4C(CH_3)_2OCH_3$ |
| —$CH_2O(CH_2)_7CH_3$ |
| —$CH(CH_3)CH_2O(CH_2)_3CH_3$ |
| —$C_2H_4O(CH_2)_5CH_3$ |
| —$C_2H_4O(CH_2)_{11}CH_3$ |

TABLE 3

[Structure: 2,6-dichloropyridine-4-yl-CH₂-O-C(=O)-R¹]

R¹

—CH₂—C₆H₅

—(CH₂)₂—C₆H₅

—CH(CH₃)—C₆H₅

—(CH₂)₃—C₆H₅

—CH(C₂H₅)—C₆H₅

—CH₂—CH(CH₃)—C₆H₅

—(CH₂)₄—C₆H₅

—CH(CH(CH₃)(C₂H₅))—C₆H₅

—CH₂—OH

—CH(CH₃)—OH

—CH₂(C₂H₅)—OH

—CH₂—CH(CH₃)—OH

—(CH₂)₃—OH

TABLE 3-continued

[Structure: 2,6-dichloropyridine-4-yl-CH₂-O-C(=O)-R¹]

R¹

—C(CH₃)(C₂H₅)—OH

—CH(CH(CH₃)₂)—OH

—C(C₂H₅)(C₂H₅)—OH

—CH₂(((CH₂)₃CH₃))—OH

—CH(C(CH₃)₃)—OH

—CH(CH₂CH(CH₃)₂)—OH

TABLE 4

[Structure: 2,6-dichloropyridine-4-yl-CH₂-O-C(=O)-R¹]

R¹

—CH₂OCH₂—C₆H₅

—CH₂OC₂H₄—C₆H₅

—CH(CH₃)OCH₂—C₆H₅

TABLE 4-continued
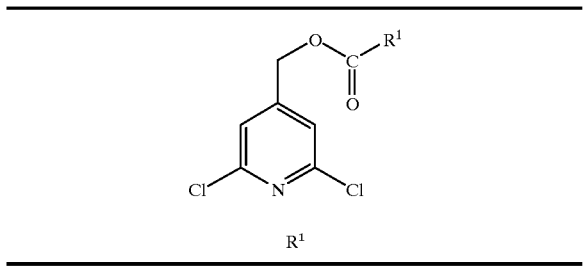
| R¹ |
|---|
| 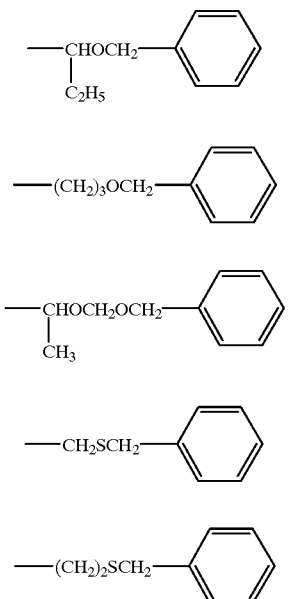 |
| 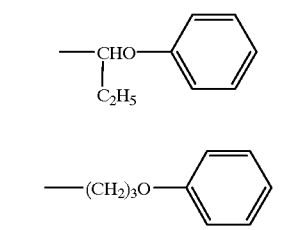 |
| 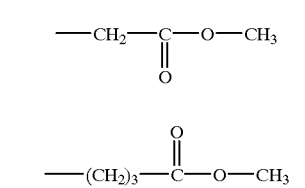 |
| 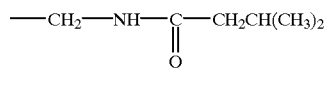 |
| 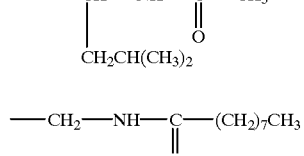 |
TABLE 4-continued
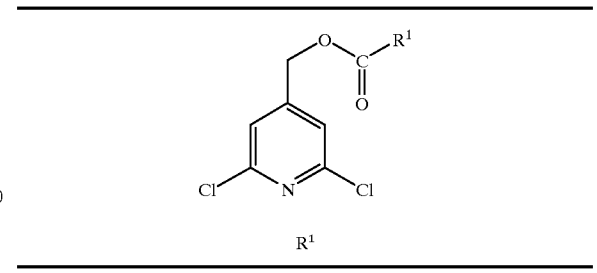
| R¹ |
|---|
| 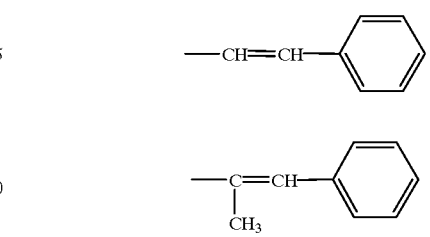 |
TABLE 5
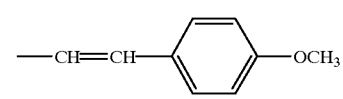
| R¹ |
|---|
| 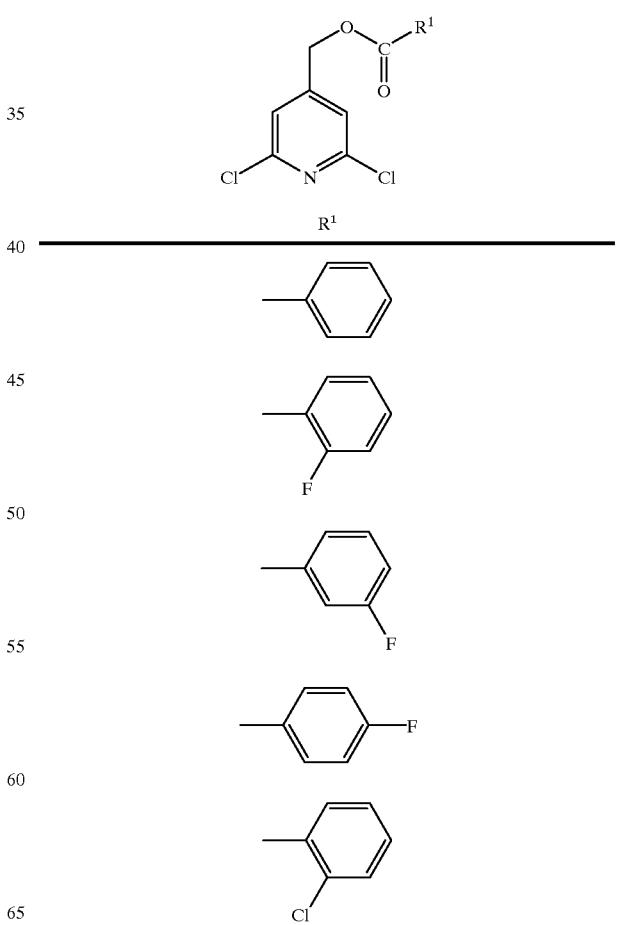 |

TABLE 5-continued
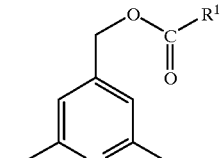
| R¹ |
|---|
| 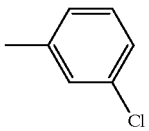 |
|  |
|  |
| 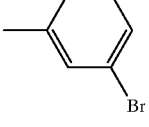 |
| 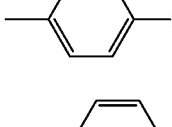 |
| 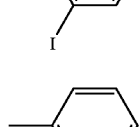 |
| 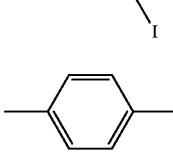 |
| 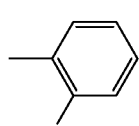 |
| 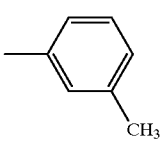 |
|  |
TABLE 5-continued
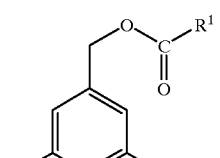
| R¹ |
|---|
| 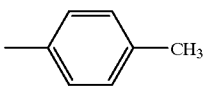 |
| 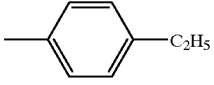 |
| 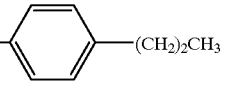 |
| 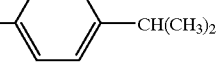 |
TABLE 6
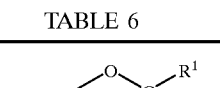
| R¹ |
|---|
| 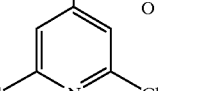 |
| 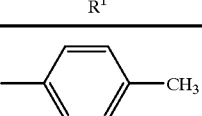 |
| 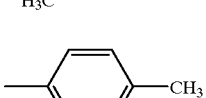 |

TABLE 6-continued
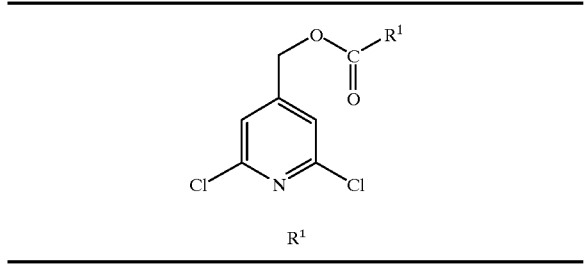
R¹
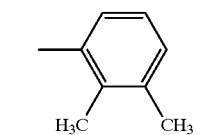
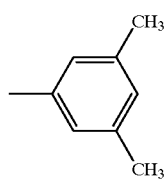
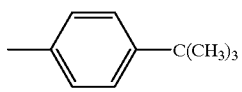
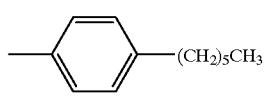
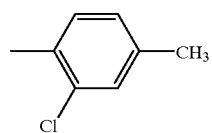
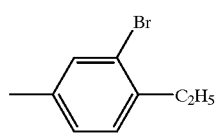
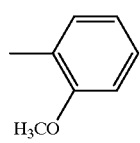
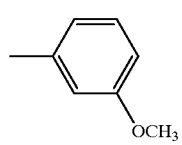
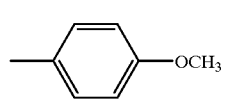
TABLE 6-continued
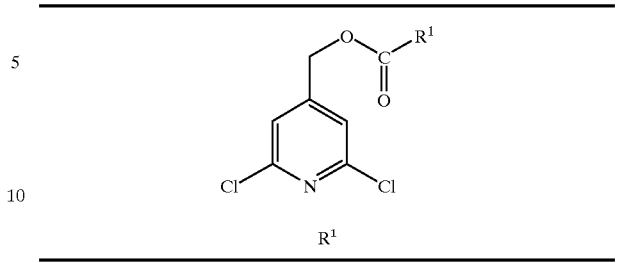
R¹
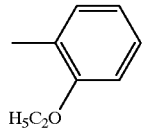
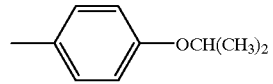
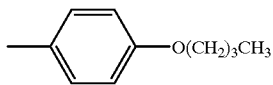
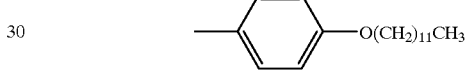
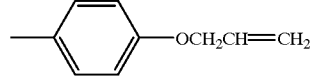
TABLE 7
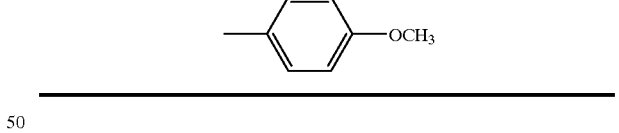
R¹
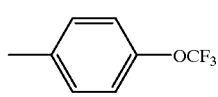

TABLE 7-continued
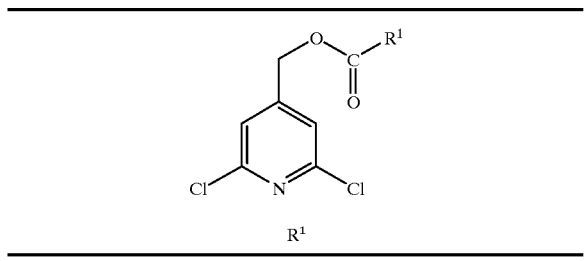
| R¹ |
|---|
| 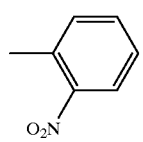 |
| 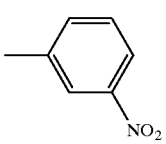 |
| 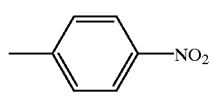 |
| 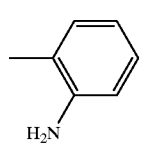 |
| 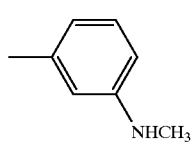 |
| 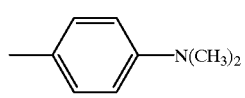 |
| 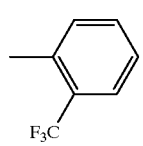 |
| 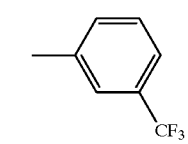 |
|  |
| 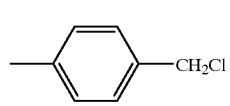 |
TABLE 7-continued
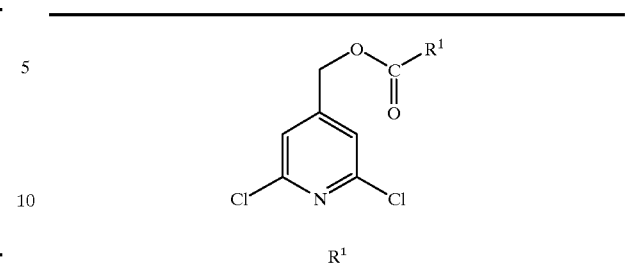
| R¹ |
|---|
| 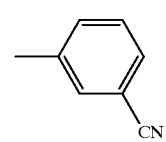 |
| 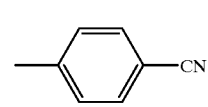 |
| 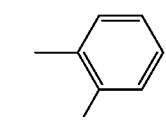 |
| 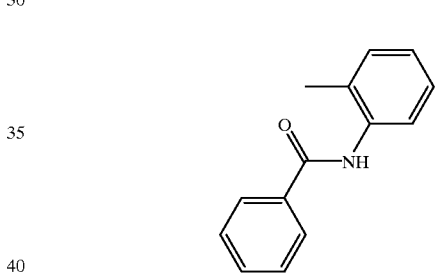 |
| 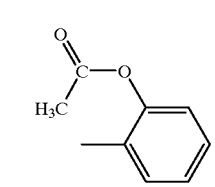 |
TABLE 8
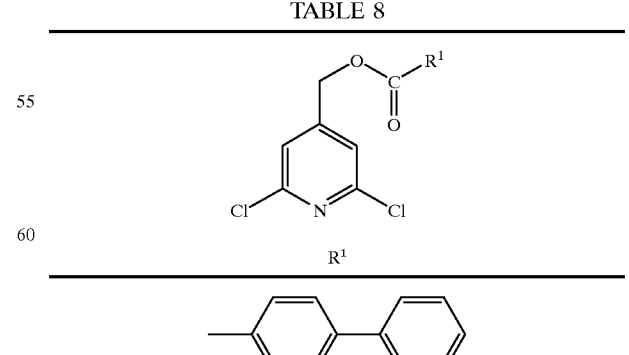
| R¹ |
|---|
| 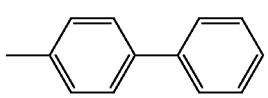 |

TABLE 8-continued
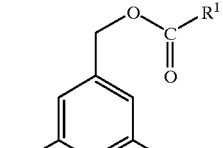
| R¹ |
|---|
| 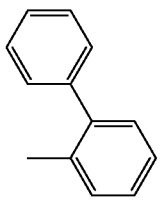 |
| 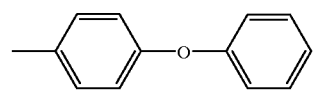 |
| 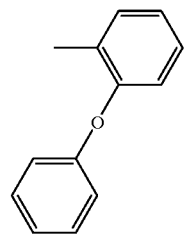 |
| 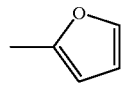 |
| 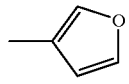 |
| 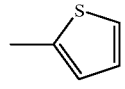 |
| 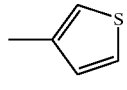 |
| 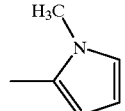 |
| 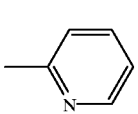 |
TABLE 8-continued
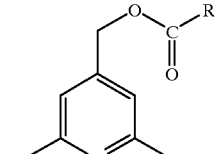
| R¹ |
|---|
| 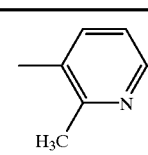 |
| 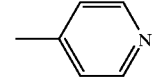 |
TABLE 9
| W |
|---|
| 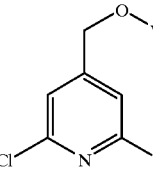 |
| 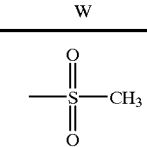 |
| —P(=O)(OCH₃)₂ |
| —P(=O)(O(CH₂)₃CH₃)₂ |
| 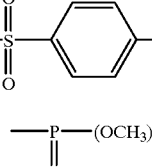 |
| 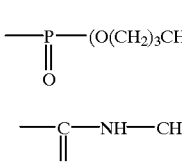 |
| 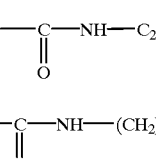 |
| 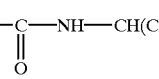 |

TABLE 9-continued

[Structure: 2,6-dichloropyridine with -CH2-O-W group at 4-position]

W

- —C(=O)—NH—phenyl
- —C(=O)—O—CH3
- —C(=O)—O—C2H5
- —C(=O)—O—(CH2)2CH3
- —C(=O)—O—CH(CH3)2
- —C(=O)—O—phenyl
- —C(=O)—C(=O)—CH3
- —C(=O)—C(=O)—C2H5
- —C(=O)—C(=O)—CH(CH3)2
- —C(=O)—C(=O)—phenyl

TABLE 10

[Structure: 2,6-dichloropyridine with -CH2-O-W group at 4-position]

W

- —Si(CH3)3
- —Si(CH3)2—C2H5
- —Si(CH3)2—(CH2)2CH3
- —Si(C2H5)3
- —Si(CH3)2—C(CH3)3
- —Si(C2H5)2—CH(CH3)2
- —Si(CH(CH3)2)3

A compound of the present invention expressed by general formula (1) can be produced by a general method employed in production of ethers or esters. For example, the compound may be produced by methods expressed by the following reaction formulae (2) to (4). However, a method for producing a compound of the present invention is not limited to these production methods. In reaction formulae (2) to (4), the meanings of W and $R^1$ are the same as the definitions of those in general formula (1), $R^8$ denotes a $C_1$ to $C_4$ alkyl group, L denotes a hydroxyl group or a halogen atom, and M denotes a hydrogen atom or a metal atom (sodium, potassium, cesium, etc.).

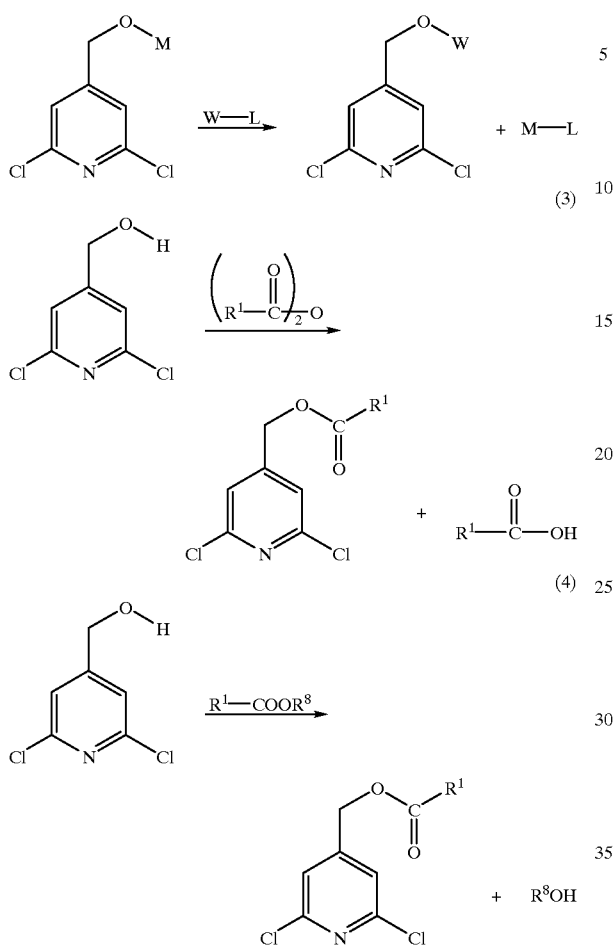

That is to say, a 2,6-dichloro-4-pyridinemethanol derivative expressed by formula (1) can be obtained by reacting 2,6-dichloro-4-pyridinemethanol or an alcoholate thereof with an alkyl halide derivative, a carboxylic acid derivative, a carboxylic acid chloride derivative, a sulfonic acid chloride derivative, a phosphoryl acid chloride derivative, a formic acid halide derivative, or a silane halide derivative, in a suitable solvent and, where necessary, in the presence of a dehydrating agent, an acid, or a base.

Alternatively, a 2,6-dichloro-4-pyridinemethanol derivative expressed by formula (1) can be obtained by reacting 2,6-dichloro-4-pyridinemethanol with a suitable halogenating agent, arylsulfonic acid, or the like to form a leaving group, and thereafter reacting with a carboxylic acid derivative, an alcohol derivative, or the like.

Alternatively, a 2,6-dichloro-4-pyridinemethanol derivative expressed by formula (1) can be obtained by adding 2,6-dichloro-4-pyridinemethanol to an olefin derivative, an isocyanate derivative, or the like in the presence of a catalyst such as an acid or a base.

As a solvent for the reaction, a hydrocarbon such as hexane, benzene, and toluene, an alcohol such as methanol and ethanol, a polyol or polyol ester such as ethylene glycol and ethylene glycol monoethyl ether, an ether such as diethyl ether and tetrahydrofuran, a hydrocarbon halide such as chloroform and dichloroethane, or an aprotic polar solvent such as N,N-dimethylformamide and dimethylsulfoxide can be used.

As a base, an organic base such as triethylamine, diisopropylethylamine, pyridine, 4-dimethylaminopyridine, and diazabicycloundecene, a hydroxide such as sodium hydroxide and potassium hydroxide, or a carbonate salt such as potassium carbonate and cesium carbonate can be used. The reaction temperature is normally in the range between −10° C. and the boiling point, although it varies depending on the solvent, the base, and the like. The reaction time is normally 0.1 to 10 hours, and preferably 0.5 to 5 hours, although it varies depending on the reaction temperature, the solvent, the base, and the like.

A method for synthesizing 2,6-dichloro-4-pyridinemethanol, which is a material for synthesizing the compound of the present invention, is disclosed, for example in J. Prakt. Chem., Vol 134, pp. 177–187 (1932).

Novel compounds of the present invention include:

a 2,6-dichloro-4-pyridinemethanol derivative in which W in general formula (1) denotes a $C_1$ to $C_8$ alkyl group or a trifluoromethylpyridyl group, the $C_1$ to $C_8$ alkyl group being unsubstituted or being substituted with an alkoxy group, an alkylthio group, a cyano group, a phenyl group, or a pyridyl group, the pyridyl group being optionally substituted with a halogen atom;

a 2,6-dichloro-4-pyridinemethanol derivative in which W in general formula (1) denotes —$SO_2R^2$ in which $R^2$ denotes a $C_1$ to $C_{12}$ alkyl group or a phenyl group which is optionally substituted with a $C_1$ to $C_{12}$ alkyl group;

a 2,6-dichloro-4-pyridinemethanol derivative in which W in general formula (1) denotes —$PO(OR^3)_2$ in which $R^3$ denotes a $C_1$ to $C_4$ alkyl group;

a 2,6-dichloro-4-pyridinemethanol derivative in which W in general formula (1) denotes —$CONHR^4$, —$COOR^4$ or —$COCOR^4$ in which $R^4$ denotes a $C_1$ to $C_3$ alkyl group or a phenyl group; and a 2,6-dichloro-4-pyridinemethanol derivative in which W in general formula (1) denotes —$SiR^5R^6R^7$ in which each of $R^5$ to $R^7$, being the same or different, denotes a $C_1$ to $C_4$ alkyl group.

Among the above 2,6-dichloro-4-pyridinemethanol derivatives, in view of the balance of agricultural chemical activity and phytotoxicity, a preferable one is a 2,6-dichloro-4-pyridinemethanol derivative in which W in general formula (1) denotes a $C_1$ to $C_8$ alkyl group or a trifluoromethylpyridyl group, the $C_1$ to $C_8$ alkyl group being unsubstituted or being substituted with an alkoxy group, an alkylthio group, a cyano group, a phenyl group, or a pyridyl group, the pyridyl group being optionally substituted with a halogen atom.

Alternatively, a novel compound of the present invention is a 2,6-dichloro-4-pyridinemethanol derivative in which W in general formula (1) denotes —$COR^1$ in which $R^1$ denotes:

a $C_1$ to $C_{18}$ alkyl group which is unsubstituted or which is substituted with an alkoxy group, an alkylthio group, a phenyl group (the phenyl group being optionally substituted with an alkoxy group), a hydroxy group, a phenylalkoxy group, a phenylalkylthio group, an alkyloxycarbonyl group, an alkylcarbonylamino group, or a phenoxy group;

a $C_1$ to $C_{18}$ alkenyl group which is unsubstituted or which is substituted with a phenyl group which is optionally substituted with an alkoxy group;

a phenyl group which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group; or a 5- or 6-membered heterocyclic ring residue which has any one of a nitrogen atom, an oxygen atom, or a sulfur atom as a ring component atom, the heterocyclic ring residue being optionally substituted with a $C_1$ to $C_4$ alkyl group.

Among these compounds, in view of the balance of agricultural chemical activity and phytotoxicity, a preferable one is a 2,6-dichloro-4-pyridinemethanol derivative in which $R^1$ is an alkenyl group which is unsubstituted or which is substituted with a phenyl group which is optionally substituted with an alkoxy group, or a 2,6-dichloro-4-pyridinemethanol derivative in which $R^1$ is a phenyl group which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group.

Among these, a 2,6-dichloro-4-pyridinemethanol derivative in which $R^1$ is a $C_1$ to $C_{12}$ alkoxyphenyl group which is optionally substituted with a halogen atom is most preferable.

An agricultural chemical, particularly an agent for controlling a plant disease, containing a 2,6-dichloro-4-pyridinemethanol derivative of the present invention as an active ingredient can be used against various plant diseases caused by viruses pathogenic to plants, by bacteria, and by molds, such as blast, which is a major disease of rice, and leaf blight of cucumbers. Such an agricultural chemical particularly exhibits great effects against blast. This agricultural chemical is believed to exhibit effects in controlling the diseases not only by the fungicidal action directly on fungi pathogenic to plants, but by the action which induces resistant reaction, which is innate to the plants, to the fungi pathogenic to the plants.

As this agricultural chemical, a 2,6-dichloro-4-pyridinemethanol derivative may be used alone. However, an agricultural chemical may be used which is prepared in the form of a wettable powder, a solution, an oil solution, a dust, a granule, a sol (a suspension concentrate), or the like by mixing a 2,6-dichloro-4-pyridinemethanol derivative with a known conventional solid or liquid carrier and an adjuvant such as a dispersant, a diluent, an emulsifier, a spreader, and a thickener.

Examples of solid or liquid carriers are talc, clay, bentonite, kaolin, diatomaceous earth, montmorillonite, mica, vermiculite, gypsum, calcium carbonate, white carbon, wood meal, starch, alumina, silicate salts, polysaccharides, wax, alcohols (such as methyl alcohol, ethyl alcohol, n-propyl alcohol, isopropyl alcohol, n-butyl alcohol, ethylene glycol, and benzyl alcohol), fractions of petroleum distillate (such as petroleum ether, kerosene, and solvent naphtha), aliphatic and alicyclic hydrocarbons (such as n-hexane and cyclohexane), aromatic hydrocarbons (such as benzene, toluene, xylene, ethylbenzene, chlorobenzene, cumene, and methylnaphthalene), hydrocarbon halides (such as chloroform and dichloromethane), ethers (such as isopropyl ether, ethylene oxide and tetrahydrofuran), ketones (such as acetone, ethyl methyl ketone, cyclohexanone, and isobutyl methyl ketone), esters (such as ethyl acetate, butyl acetate, ethylene glycol acetate, and amyl acetate), acid amides (such as dimethylformamide and dimethylacetanilide), nitriles (such as acetonitrile, propionitrile, and acrylonitrile), sulfoxides (such as dimethyl sulfoxide), and alcohol ethers (such as ethylene glycol monomethyl ether and ethylene glycol monoethyl ether).

Examples of adjuvants are nonionic surface active agents (such as polyoxyethylene alkyl ethers, polyoxyethylene alkyl esters, polyoxyethylene alkylphenyl ethers, polyoxyethylene sorbitan alkyl ethers, and sorbitan alkyl esters), anionic surface active agents (such as alkylbenzenesulfonates, alkylsulfosuccinates, polyoxyethylene alkyl sulfates, and arylsulfonates), cationic surface active agents (such as alkylamines, polyoxyethylenealkylamines, and quaternary ammonium salts), amphoteric surface active agents (such as alkylaminoethylglycine and alkyldimethylbetaine), polyvinyl alcohol, hydroxypropyl cellulose, carboxymethyl cellulose, gum arabic, tragacanth gum, xanthane gum, polyvinyl acetate, gelatin, casein, and sodium alginate.

In addition, the agricultural chemical of the present invention may be used in a mixture with any of various agricultural chemicals (such as fungicides for agricultural and horticultural use, herbicides, plant growth regulators, insecticides, and acaricides) and fertilizers. The amount of the active ingredient in the agricultural chemical of the present invention is normally 0.5 to 95% by weight, and preferably 1 to 50% by weight, although the amount varies depending on the prepared form, the process of application, and other conditions.

In the process of application of the agricultural chemical of the present invention, the agricultural chemical may be applied to plants (foliage application), soil on which plants grow (soil application), paddy surface water (water surface application), seeds (seed treatment), or the like.

A suitable amount of the agricultural chemical of the present invention used per 10 ares, although it varies depending on the plant to which the agricultural chemical is applied and on the disease of the plant, is 50 to 300 L of a solution having 1 to 10000 ppm, preferably 10 to 1000 ppm, of the active ingredient in the case of foliage application, and 0.1 g to 1000 g, preferably 10 to 100 g, of the active ingredient in the case of soil application or water surface application. In the case of seed treatment, 0.001 to 50 g of the active ingredient per 1 kg of seeds are preferable.

A 2,6-dichloro-4-pyridinemethanol derivative according to the present invention does not have the possibility of being phytotoxic for plants, and is greatly effective in controlling various plant diseases caused by viruses pathogenic to plants, by bacteria, and by molds, as it is useful as an agent for controlling plant diseases.

EXAMPLES

The present invention will be explained in the following by way of examples, formulation examples, and test examples. However, the present invention should not be limited to these.

Example 1

0.18 g of 2,6-dichloro-4-pyridinemethanol were dissolved into 5 ml of tetrahydrofuran (hereinafter referred to as "THF"), the solution was cooled by ice, and thereafter 0.04 g of sodium hydride (oil base, 60%) were added. To this, a solution of 0.15 g of methyl iodide dissolved in 2 ml of THF was added dropwise, and stirring was conducted for 2 hours at room temperature. Ethyl acetate was added to the reacted solution, and after the organic phase was washed by water, the organic phase was dried by adding sodium sulfate. The solvent was removed by evaporation, and the residue was purified by silica gel column chromatography to obtain 0.06 g of 2,6-dichloro-4-methoxymethylpyridine (Compound No. 1).

Nuclear magnetic resonance spectrum (internal standard: TMS; solvent: $CDCl_3$) (ppm): 3.46 (s,3H), 4.45 (s,2H), 7.25 (s,2H)

Example 2

0.36 g of 2,6-dichloro-4-pyridinemethanol and 0.1 g of triethylamine were dissolved into 2 ml of THF, 0.12 g of acrylonitrile were added to the solution at room temperature, and stirring was conducted for 2 hours. After the reacted solution was left overnight at room temperature, ethyl acetate was added. The organic phase was washed with water, and was dried by adding sodium sulfate. The solvent was removed by evaporation, and the residue was purified by silica gel column chromatography to obtain 0.23 g of 2,6-dichloro-4-(2-cyanoethoxymethyl)pyridine (Compound No. 6).

Melting point: 65.5° C.

Mass spectrum: 230, 232, 161, 163

Example 3

3.56 g of 2,6-dichloro-4-pyridinemethanol and 4 ml of pyridine were dissolved into 20 ml of THF, a solution of 0.8 ml of thionyl chloride dissolved in 12 ml of dichloromethane was added thereto dropwise, and stirring was conducted for 2 hours. Subsequently, this was heated and refluxed for 1 hour, and after cooling, diethylether was added thereto for extraction. The organic phase was washed with water, and was dried by adding sodium sulfate. The solvent was removed by evaporation, and the residue was purified by silica gel column chromatography to obtain 2.31 g of bis(2,6-dichloro-4-pyridylmethyl) ether (Compound No. 11).

Melting point: 69.1° C.

Mass spectrum: 337, 336, 338, 161, 160, 162, 309

Example 4

0.09 g of 2,6-dichloro-4-pyridinemethanol and 0.51 g of triethylamine were dissolved into 5 ml of THF, a solution of 0.31 g of acetyl chloride dissolved in 2 ml of THF was added thereto under ice-cold conditions, and stirring was conducted for 2 hours. After the reacted solution was left overnight at room temperature, ethyl acetate was added. The organic phase was washed with water, and was dried by adding sodium sulfate. The solvent was removed by evaporation, and the residue was purified by silica gel column chromatography to obtain 0.10 g of (2,6-dichloro-4-pyridinyl)methyl acetate ester (Compound No. 13).

Example 5

0.36 g of 2,6-dichloro-4-pyridinemethanol and 0.30 g of 4-methylbenzoic acid were dissolved into 5 ml of THF, 0.44 g of 1-ethyl-3-(3-dimethylaminopropyl)carbodiamide hydrochloride and 0.56 g of 4-dimetylaminopyridine were added thereto, and stirring was conducted for 2 hours. After the reacted solution was left overnight at room temperature, ethyl acetate was added. The organic phase was washed with water, and was dried by adding sodium sulfate. The solvent was removed by evaporation, and the residue was purified by silica gel column chromatography to obtain 0.36 g of (2,6-dichloro-4-pyridinyl)methyl 4-methylbenzoate ester (Compound No. 45).

Example 6

1.4 g of 2,6-dichloro-4-pyridinemethanol were dissolved into 5 ml of pyridine, and the solution was cooled by ice. To this, 1.5 g of 2-nitrobenzoyl chloride, which was prepared from 2-nitrobenzoic acid and thionyl chloride, were added dropwise. After the reacted solution was stirred for 2 hours, dichloromethane was added. The organic phase was washed with water, and was dried by adding sodium sulfate. The solvent was removed by evaporation, and the residue was purified by silica gel column chromatography to obtain 1.4 g of (2,6-dichloro-4-pyridinyl)methyl 2-nitrobenzoate ester (Compound No. 69).

Example 7

0.36 g of 2,6-dichloro-4-pyridinemethanol and 0.40 g of triethylamine were dissolved into 4 ml of THF, and the solution was cooled by ice. To this, a solution of 0.42 g of 4-methylbenzenesulfonyl chloride monohydrate dissolved in 2 ml of THF was added dropwise. After the reacted solution was stirred for 2 hours, diethyl ether was added. The organic phase was washed with water, and was dried by adding sodium sulfate. The solvent was removed by evaporation, and the residue was purified by silica gel column chromatography to obtain 0.43 g of (2,6-dichloro-4-pyridinyl)methyl 4-methylbenzenesulfonate ester (Compound No. 89).

Example 8

0.25 g of 2,6-dichloro-4-pyridinemethanol were dissolved into 1 ml of pyridine, and the solution was cooled by ice. To this, 0.15 ml of phenyl isocyanate were added dropwise. After the reacted solution was stirred for 2 hours, dichloromethane was added. The organic phase was washed with water, and was dried by adding sodium sulfate. The solvent was removed by evaporation, and the residue was purified by silica gel column chromatography to obtain 0.20 g of (2,6-dichloro-4-pyridinyl)methyl phenylcarbamate ester (Compound No. 93).

Example 9

0.35 g of 2,6-dichloro-4-chloromethylpyridine, 0.31 g of benzoyl formate, and 0.19 g of sodium hydrogencarbonate were added to 5.0 ml of dimethylformamide, and heating and stirring were conducted at 70° C. for 4 hours. After cooling, ethyl acetate was added to the reacted solution. The organic phase was washed with water, and was dried by adding sodium sulfate. The solvent was removed by evaporation, and the residue was purified by silica gel column chromatography to obtain 0.18 g of (2,6-dichloro-4-pyridinyl)methyl benzoylformate ester (Compound No. 95).

Reference Example

Production of 2,6-dichloro-4-chloromethylpyridine 5.0 g of 2,6-dichloro-4-pyridinemethanol and 2.5 ml of pyridine were suspended in 10 ml of toluene, and the suspension was cooled in a salt-ice bath. To this, 2.7 ml of thionyl chloride were added dropwise for 1 hour, and subsequently the reacted solution was stirred at 110° C. for 3 hours. After cooling, water was added to the solution, and extraction was conducted using diethyl ether. The organic phase was washed with water, and was dried by adding sodium sulfate. The solvent was removed by evaporation, and the residue was purified by silica gel column chromatography to obtain 5.0 g of 2,6-dichloro-4-chloromethylpyridine.

Example 10

0.30 g of 2,6-dichloro-4-chloromethylpyridine and 0.25 g of tert-butyldimethylsilyl chloride were added to 4.0 ml of dimethylformamide, and were dissolved. The solution was cooled in an ice bath. After 0.14 g of imidazole was added, stirring was conducted at room temperature for 5.5 hours. Ethyl acetate was added to the reacted solution. The organic phase was washed with water, and was dried by adding sodium sulfate. The solvent was removed by evaporation, and the residue was purified by silica gel column chromatography to obtain 0.41 g of 2,6-dichloro-4-((1,1-dimethylethyl)dimethylsilyl)oxymethylpyridine (Compound No. 96).

Examples 11–96

In the same manner as in Examples 1 to 10, Compounds Nos. 2 to 5, 7 to 10, 12, 14 to 44, 46 to 68, 70 to 88, 90 to 92, and 94 shown in Tables 11 to 27 were obtained.

TABLE 11

| Compound No. | W | Physical Property |
|---|---|---|
| 1 | —CH$_3$ | $^1$H-NMR(CDCl$_3$, δ[ppm]) 3.46(s, 3H), 4.45(s, 2H), 7.25 (s, 2H) MS: 191, 193, 161, 163, 126 |
| 2 | —CH(CH$_3$)$_2$ | $^1$H-NMR(CDCl$_3$, δ[ppm]) 1.12(d, 6H), 3.65(m, 1H), 4.43 (s, 2H), 7.20(s, 2H) |
| 3 | —(CH$_2$)$_7$CH$_3$ | $^1$H-NMR(CDCl$_3$, δ[ppm]) 0.8–1.6(m, 15H), 3.68(t, 2H), 4.41(s, 2H), 7.15(s, 2H) |
| 4 | —(CH$_2$)$_2$OCH$_3$ | $^1$H-NMR(CDCl$_3$, δ[ppm]) 3.39(s, 3H), 3.60–3.75(m, 4H), 4.48(s, 2H), 7.21(s, 2H) |
| 5 | —(CH$_2$)$_2$SCH$_3$ | $^1$H-NMR(CDCl$_3$, δ[ppm]) 3.44(s, 3H), 2.85–3.05(m, 4H), 4.43(s, 2H), 7.18(s, 2H) |
| 6 | —(CH$_2$)$_2$CN | m.p. 65.5° C. MS: 230, 232, 161, 163 |
| 7 | —(CH$_2$)$_3$CN | $^1$H-NMR(CDCl$_3$, δ[ppm]) 2.15(m, 2H), 2.59(t, 2H), 3.61 (t, 2H), 4.40(s, 2H), 7.25(s, 2H) |

TABLE 12

| Compound No. | W | Physical Property |
|---|---|---|
| 8 | —CH$_2$—phenyl | $^1$H-NMR(CDCl$_3$, δ[ppm]) 4.51(s, 2H), 4.62(s, 2H), 7.26(s, 2H), 7.37(m, 5H) MS: 161, 163, 91 |
| 9 | —(CH$_2$)$_2$—phenyl | $^1$H-NMR(CDCl$_3$, δ[ppm]) 2.95(t, 2H), 4.53(t, 2H), 4.65(s, 2H), 7.29(s, 2H), 7.35(m, 5H) MS: 161, 163, 91 |
| 10 | —CH$_2$—(3-pyridyl) | $^1$H-NMR(CDCl$_3$, δ[ppm]) 4.60(s, 2H), 4.95(s, 2H), 7.2–8.3(m, 6H) |
| 11 | —CH$_2$—(2,6-dichloro-4-pyridyl) | m.p. 69.1° C. MS: 337, 336, 338, 161, 160, 162, 309 |
| 12 | —(6-methyl-3-CF$_3$-pyridyl) | m.p. 49.8° C. $^1$H-NMR(CDCl$_3$, δ[ppm]) 5.46(s, 2H), 7.00(d, 1H), 7.33(s, 2H), 7.88(d, 1H), 8.47(s, 1H) MS: 322, 334, 147, 176 |

TABLE 13

| Compound No. | R$^1$ | Physical Property |
|---|---|---|
| 13 | —CH$_3$ | nD21.0: 1.5357 $^1$H-NMR (CDCl$_3$, δ[ppm]) 2.18(s, 3H), 5.10(s, 2H), 7.24(s, 2H) |
| 14 | —(CH$_2$)$_6$CH$_3$ | m.p. 27.2° C. $^1$H-NMR (CDCl$_3$, δ[ppm]) 0.70–2.80 (m, 15H), 5.10(s, 2H) |

TABLE 13-continued

| Compound No. | R¹ | Physical Property |
|---|---|---|
|  |  | 7.24(s, 2H)<br>MS: 304, 306, 268, 184 |
| 15 | —(CH₂)₁₇CH₃ | ¹H-NMR (CDCl₃, δ[ppm])<br>0.85–2.31 (m, 37H),<br>5.15(s, 2H)<br>7.21(s, 2H) |
| 16 | 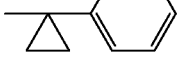 | m.p. 48.7° C.<br>MS: 245, 247, 160, 167 |
| 17 | —(CH₂)₇CH=CH(CH₂)₇CH₃ | Oil |
| 18 | —CH=CH—CH=CH—CH₃ | m.p. 119.9° C. |
| 19 | —(CH₂)₇CH=CHCH₂CH=CH—(CH₂)₄CH₃ | Oil |
| 20 | —(CH₂)₂OC₂H₅ | nD20.0: 1.5152<br>MS: 2.78, 280, 248, 250, 232, 234 |
| 21 | —CH₂O(CH₂)₃CH₃ | nD20.2: 1.5060<br>MS: 292, 294 |

TABLE 14

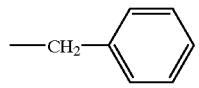

| Compound No. | R¹ | Physical Property |
|---|---|---|
| 22 | —(CH₂)₂SCH₃ | ¹H-NMR(CDCl₃, δ[ppm])<br>2.12(s, 3H), 2.62(t, 2H),<br>2.77(t, 2H), 5.12(s, 2H),<br>7.24(s, 2H) |
| 23 | —CH₂O(CH₂)₁₁CH₃ | ¹H-NMR(CDCl₃, δ[ppm])<br>0.8–1.7(m, 23H), 3.47(t, 2H),<br>4.21(s, 2H), 5.19(s, 2H),<br>7.21(s, 2H) |
| 24 | —CH₂—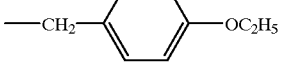 | ¹H-NMR(CDCl₃, δ[ppm])<br>3.59(s, 2H), 5.20(s, 2H),<br>7.1–7.3(m, 7H) |

TABLE 14-continued

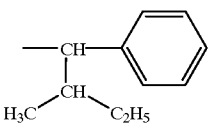

| Compound No. | R¹ | Physical Property |
|---|---|---|
| 25 | 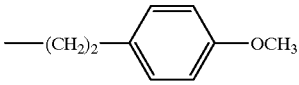 | ¹H-NMR(CDCl₃, δ[ppm])<br>0.6–2.2(m, 9H), 3.25(d, 1H),<br>5.22(s, 2H), 7.0–7.3(m, 7H) |

TABLE 15

| Compound No. | R¹ | Physical Property |
|---|---|---|
| 26 | 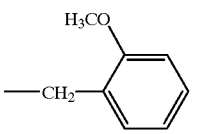 | m.p. 95.2° C.<br>MS: 323, 321 |
| 27 | —CH₂—⟨ ⟩—OC₂H₅ | nD20.5: 1.5643<br>¹H-NMR(CDCl₃, δ[ppm])<br>1.41(t, 3H),<br>3.66(s, 2H), 4.03 (q, 2H), 5.08(s, 2H),<br>6.88(d, 2H),<br>7.07(s, 2H),<br>7.20(d, 2H) |
| 28 | —(CH₂)₂—⟨ ⟩—OCH₃ | MS: 341, 339 |
| 29 | H₃CO—⟨ ⟩—CH₂— 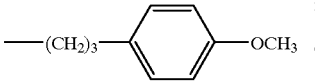 | MS: 341, 339 |
| 30 | —(CH₂)₃—⟨ ⟩—OCH₃ | m.p. 50.1° C.<br>¹H-NMR(CDCl₃, δ[ppm])<br>1.98(m, 2H),<br>2.40(t, 2H),<br>2.60(t, 2H),<br>3.79(s, 3H), 5.06 (s, 2H), 6.80(d, 2H),<br>7.07(d, 2H),<br>7.21(s, 2H) |

TABLE 16

Structure: 2,6-dichloropyridin-4-yl-methyl ester of R¹COO-

| Compound No. | R¹ | Physical Property |
|---|---|---|
| 31 | —CH=CH—(phenyl) | m.p. 237.8° C. ¹H-NMR(CDCl₃, δ[ppm]) 5.22(s, 2H), 6.52(d, 1H), 7.82(d, 2H), 7.29(s, 2H), 7.3–7.7(m, 5H) MS: 307, 309, 262, 264, 131 |
| 32 | —CH=CH—(4-OCH₃-phenyl) | m.p. 99.8° C. ¹H-NMR(CDCl₃, δ[ppm]) 3.85(s, 3H), 5.23(s, 2H), 6.50(d, 1H), 7.0–7.4(m, 6H), 7.75(d, 1H) |
| 33 | —CH=CH—(3-OCH₃-phenyl) | m.p. 111.7° C. ¹H-NMR(CDCl₃, δ[ppm]) 3.85(s, 3H), 5.23(s, 2H), 6.51(d, 1H), 7.0–7.4(m, 6H), 7.75(d, 1H) |
| 34 | —CH=CH—(2-OCH₃-phenyl) | m.p. 135.3° C. ¹H-NMR(CDCl₃, δ[ppm]) 3.91(s, 3H), 5.22(s, 2H), 6.62(d, 1H), 6.9–7.6(m, 6H), 8.09(d, 1H) |

TABLE 17

Structure: 2,6-dichloropyridin-4-yl-methyl ester of R¹COO-

| Compound No. | R¹ | Physical Property |
|---|---|---|
| 35 | —CHOH—CH₃ | MS: 249, 251 |
| 36 | —CH₂—CHOH—(CH₂)₂CH₃ | ¹H-NMR(CDCl₃, δ[ppm]) 0.92(t, 3H), 1.3–1.6(m, 4H), 2.3–2.6(m, 2H), 4.00(m, 1H), 5.25(s, 2H), 7.1–7.4(m, 7H) |
| 37 | —CH₂OCH₂—(phenyl) | ¹H-NMR(CDCl₃, δ[ppm]) 3.80(s, 2H), 4.54(s, 2H), 5.23(s, 2H), 7.0–7.4(m, 7H) |
| 38 | —(CH₂)₂SCH₂—(phenyl) | ¹H-NMR(CDCl₃, δ[ppm]) 3.5–3.7(m, 4H), 3.82(s, 2H), 5.21(s, 2H), 7.0–7.3(m, 7H) |
| 39 | —CH(CH₃)OCH₂—(phenyl) | MS: 263, 265 |
| 40 | —CH(C₂H₅)—O—(phenyl) | m.p. 85.4° C. ¹H-NMR(CDCl₃, δ[ppm]) 1.11(t, 3H), 2.04(m, 2H), 4.70(t, 1H), 5.04(d, 1H), 5.19(d, 1H), 6.8–7.0(m, 5H), 7.2–7.3(m, 2H) |

TABLE 18

Structure: 2,6-dichloropyridin-4-yl-methyl ester of R¹COO-

| Compound No. | R¹ | Physical Property |
|---|---|---|
| 41 | —CH₂—C(=O)—O—CH₃ | MS: 277, 279 |

TABLE 18-continued

Structure: 2,6-dichloropyridin-4-yl-methyl ester of R¹ (—CH₂—O—C(=O)—R¹)

| Compound No. | R¹ | Physical Property |
|---|---|---|
| 42 | —(CH₂)₃—C(=O)—O—CH₃ | ¹H-NMR(CDCl₃, δ[ppm]) 1.95(m, 2H), 2.3–2.5(m, 4H), 3.70(s, 3H), 5.24(s, 2H), 7.24(s, 2H) |
| 43 | —CH₂—NH—C(=O)—CH₃ | m.p. 96.5° C. MS: 276, 278 |
| 44 | —CH₂—NH—C(=O)—(CH₂)₇CH₃ | ¹H-NMR(CDCl₃, δ[ppm]) 0.89(m, 3H), 1.2–2.0(m, 12H), 3.79(d, 2H), 5.21(s, 2H), 7.25(s, 2H) |

TABLE 19

Structure: 2,6-dichloropyridin-4-yl-methyl ester of R¹

| Compound No. | R¹ | Physical Property |
|---|---|---|
| 45 | 4-methylphenyl | m.p. 116.9° C. MS: 295, 297, 135 |
| 46 | 3-methylphenyl | m.p. 92.9° C. MS: 295, 297, 135 |
| 47 | 2-methylphenyl | m.p. 125.3° C. MS: 295, 297, 135 |
| 48 | 4-(n-hexyl)phenyl —(CH₂)₅CH₃ | m.p. 79.5° C. MS: 365, 367, 294, 296, 189 |

TABLE 19-continued

| Compound No. | R¹ | Physical Property |
|---|---|---|
| 49 | 4-chlorophenyl | m.p. 137.8° C. MS: 315, 317, 139 |
| 50 | 3-chlorophenyl | m.p. 120.5° C. MS: 315, 317, 139 |
| 51 | 2-chlorophenyl | m.p. 145.7° C. MS: 315, 317, 139 |

TABLE 20

Structure: 2,6-dichloropyridin-4-yl-methyl ester of R¹

| Compound No. | R¹ | Physical Property |
|---|---|---|
| 52 | 4-methoxyphenyl | m.p. 121.8° C. MS: 311, 313, 135 |
| 53 | 3-methoxyphenyl | m.p. 237.9° C. MS: 311, 313, 135 |
| 54 | 2-methoxyphenyl | m.p. 116.2° C. MS: 311, 313, 135 |
| 55 | 4-ethoxyphenyl —OC₂H₅ | m.p. 143.1° C. MS: 325, 327, 149, 121 |

TABLE 20-continued

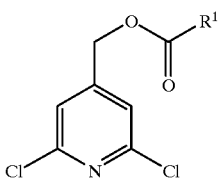

| Compound No. | R¹ | Physical Property |
|---|---|---|
| 56 | 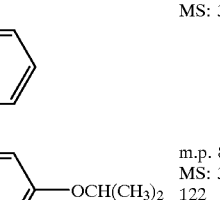 (2-ethoxyphenyl, H₅C₂O-) | m.p. 86.1° C. MS: 325, 327, 121, 147 |
| 57 | 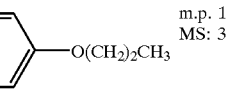 (4-OCH(CH₃)₂-phenyl) | m.p. 89.6° C. MS: 339, 341, 297, 299, 122 |
| 58 | 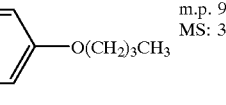 (4-O(CH₂)₂CH₃-phenyl) | m.p. 114.0° C. MS: 339, 341, 122 |
| 59 | 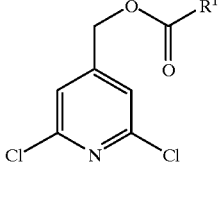 (4-O(CH₂)₃CH₃-phenyl) | m.p. 97.0° C. MS: 353, 355, 122 |

TABLE 21

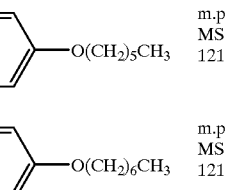

| Compound No. | R¹ | Physical Property |
|---|---|---|
| 60 | 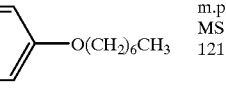 (4-O(CH₂)₄CH₃-phenyl) | m.p. 83.0° C. MS: 367, 369, 298, 300, 122 |
| 61 | 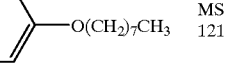 (4-O(CH₂)₅CH₃-phenyl) | m.p. 92.2° C. MS: 381, 383, 298, 300, 121 |
| 62 | 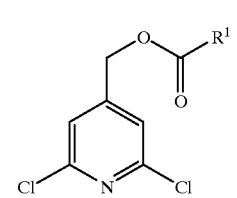 (4-O(CH₂)₆CH₃-phenyl) | m.p. 87.5° C. MS: 395, 397, 298, 300, 121 |
| 63 | 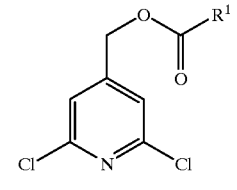 (4-O(CH₂)₇CH₃-phenyl) | m.p. 91.4° C. MS: 409, 411, 298, 300, 121 |

TABLE 21-continued

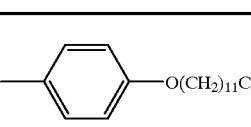

| Compound No. | R¹ | Physical Property |
|---|---|---|
| 64 | 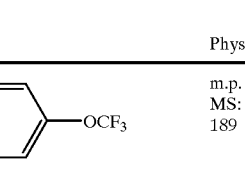 (4-O(CH₂)₁₁CH₃-phenyl) | m.p. 90.7° C. MS: 465, 467, 298, 300, 121 |

TABLE 22

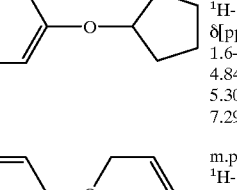

| Compound No. | R¹ | Physical Property |
|---|---|---|
| 65 | 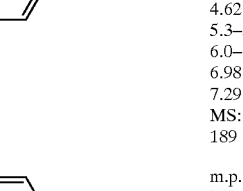 (4-OCF₃-phenyl) | m.p. 80.6° C. MS: 365, 367, 280, 282, 189 |
| 66 | 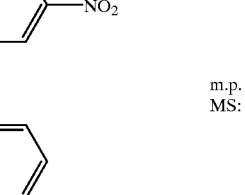 (4-O-cyclopentyl-phenyl) | m.p. 103.2° C. ¹H-NMR(CDCl₃, δ[ppm]) 1.6–2.0(m, 8H), 4.84(m, 1H), 5.30(s, 2H), 6.92(d, 2H), 7.29(s, 2H), 8.01 (d, 2H) |
| 67 |  (4-O-allyl-phenyl) | m.p. 106.1° C. ¹H-NMR(CDCl₃, δ[ppm]) 4.62(d, 2H), 5.30(s, 2H), 5.3–5.5(m, 2H), 6.0–6.1(m, 1H), 6.98(d, 2H), 7.29(s, 2H), 8.03(d, 2H) MS: 365, 367, 280, 282, 189 |
| 68 |  (4-NO₂-phenyl) | m.p. 148.1° C. MS: 326, 328, 150 |
| 69 |  (2-NO₂-phenyl) | m.p. 108.4° C. MS: 326, 328, 150 |

TABLE 23

| Compound No. | R¹ | Physical Property |
|---|---|---|
| 70 | 4-N(CH₃)₂-phenyl-methyl | m.p. 162.5° C. MS: 324, 326, 148 |
| 71 | 4-CN-phenyl-methyl | m.p. 181.4° C. MS: 306, 308, 130 |
| 72 | 4-CF₃-phenyl-methyl | m.p. 112.7° C. MS: 349, 351, 330, 332, 173 |
| 73 | 3-CF₃-phenyl-methyl | m.p. 94.1° C. MS: 349, 351, 330, 332, 173 |
| 74 | 2-CF₃-phenyl-methyl | m.p. 72.1° C. MS: 349, 351, 330, 332, 173 |

TABLE 24

| Compound No. | R¹ | Physical Property |
|---|---|---|
| 75 | 2-H₂N-phenyl-methyl | m.p. 175.4° C. MS: 296, 298 |
| 76 | 2-(CH₃C(O)NH)-phenyl-methyl | m.p. 162.8° C. MS: 338, 340 |

TABLE 24-continued

| Compound No. | R¹ | Physical Property |
|---|---|---|
| 77 | 2-(PhC(O)NH)-phenyl-methyl | m.p. 177.9° C. MS: 400, 402 |
| 78 | 2,6-difluoro-phenyl-methyl | m.p. 103.7° C. MS: 317, 319, 142 |
| 79 | 3,4-dichloro-phenyl-methyl | m.p. 123.8° C. MS: 353, 351, 349, 173 |
| 80 | 2-(CH₃C(O)O)-phenyl-methyl | m.p. 91.6° C. MS: 297, 299, 120 |

TABLE 25

| Compound No. | R¹ | Physical Property |
|---|---|---|
| 81 | 2-phenoxy-phenyl-methyl | m.p. 70.5° C. MS: 373, 375, 280, 282, 197 |

TABLE 25-continued

Structure: 2,6-dichloropyridine with 4-CH₂-O-C(=O)-R¹

| Compound No. | R¹ | Physical Property |
|---|---|---|
| 82 | 2-methylbiphenyl | MS: 357, 359, 181, 152 |
| 83 | 2-thienyl | m.p. 116.6° C.<br>MS: 287, 289, 111 |
| 84 | 3-furyl | MS: 271, 273, 95 |
| 85 | 4-pyridyl | m.p. 164.4° C.<br>MS: 282, 284, 107 |
| 86 | 2-methyl-3-pyridyl | MS: 296, 298, 121 |

TABLE 26

Structure: 2,6-dichloropyridine with 4-CH₂-O-W

| Compound No. | W | Physical Property |
|---|---|---|
| 87 | -S(=O)₂-CH₃ | m.p. 103.8° C.<br>MS: 255, 257, 176, 174 |
| 88 | -S(=O)₂-(CH₂)₁₁CH₃ | oil |

TABLE 26-continued

Structure: 2,6-dichloropyridine with 4-CH₂-O-W

| Compound No. | W | Physical Property |
|---|---|---|
| 89 | -S(=O)₂-C₆H₄-4-CH₃ | m.p. 64.9° C.<br>MS: 331, 333, 171, 91 |
| 90 | -S(=O)₂-C₆H₄-4-C₁₂H₂₅ | oil |
| 91 | -P(=O)(O(CH₂)₃CH₃)(O(CH₂)₃CH₃) | m.p. 73.5° C. |
| 92 | -C(=O)-NH-(CH₂)₂CH₃ | m.p. 71.3° C. |

TABLE 27

Structure: 2,6-dichloropyridine with 4-CH₂-O-W

| Compound No. | W | Physical Property |
|---|---|---|
| 93 | -C(=O)-NH-C₆H₅ | m.p. 154.0° C. |
| 94 | -C(=O)-O-C₆H₅ | m.p. 84.8° C. |
| 95 | -C(=O)-C(=O)-C₆H₅ | m.p. 92.5° C.<br>MS: 207 |

TABLE 27-continued

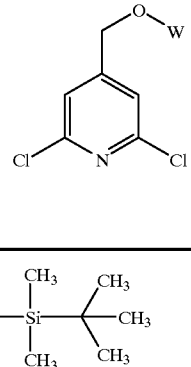

| Compound No. | W | Physical Property |
|---|---|---|
| 96 | 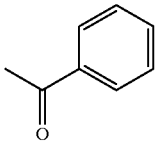 | m.p. 63.2° C.<br>MS: 291 293 |
| 97 | —H | m.p. 131° C. |
| 98 | (phenyl ketone structure) | m.p. 119° C. |

In Table 27, Compounds Nos. 97 and 98 are known compounds.

Formulation Example 1

Dust 2 parts by weight of each of 2,6-dichloro-4-pyridinemethanol derivatives indicated as Compounds Nos. 1 to 98 were mixed and crushed with 98 parts by weight of clay to form dust.

Formulation Example 2

Wettable Powder 20 parts by weight of each of 2,6-dichloro-4-pyridinemethanol derivatives indicated as Compounds Nos. 1 to 98 were mixed and crushed with 68 parts by weight of clay, 8 parts by weight of white carbon, and 4 parts by weight of polyoxyethylene nonylphenyl ether to form wettable powder.

Formulation Example 3

Granules 5 parts by weight of each of 2,6-dichloro-4-pyridinemethanol derivatives indicated as Compounds Nos. 1 to 98 were mixed and crushed with 90 parts by weight of mixture of bentonite and talc in equivalent amounts and 5 parts by weight of sodium alkylbenzenesulfonate, and the mixture was molded into granules.

Test Example 1

Test for Rice Blast Control (Water Surface Application)

Chemical solutions prepared by diluting each wettable powder described in "Formulation Example 2" in water were applied to rice plants (cultivar: Aichiasahi) in the two-leaf stage planted in pots (diameter: 6 cm; height: 5.5 cm) by way of water surface application (amount of active ingredient: 0.01 mg/pot). Fourteen days later, a suspension of spores of rice blast fungus (Pyricularia oryzae) was sprayed for inoculation. After the rice plants were left in a moist chamber at 25° C. for 24 hours, they were kept in a greenhouse. The number of lesions was investigated 10 days after the inoculation.

Tests were also conducted in a similar manner using the same amount of active ingredients, but using, as controls, propenazole granules which are commercially sold as an agent for controlling rice blast (active ingredient: 8%) and 2,6-dichloronicotinic acid (a compound disclosed in Japanese Patent No 2514823). Protective values were calculated according to the following formula. In addition, foliage die back and growth retardation of the plants were observed for phytoxicity. The results are shown in Table 28. In the table, the minus sign (−) indicates that no phytotoxicity was observed, and the plus sign (+) indicates that phytoxicity was observed.

$$\text{Protective value (\%)} = \frac{\text{(no. of lesions in untreated group)} - \text{(no. of lesions in treated group)}}{\text{no. of lesions in untreated group}} \times 100$$

TABLE 28

| Compound No. | Protective value (%) | Foliage die back | Growth retardation of plants |
|---|---|---|---|
| 1 | 81 | − | − |
| 6 | 88 | − | − |
| 8 | 81 | − | − |
| 13 | 86 | − | − |
| 16 | 87 | − | − |
| 18 | 99 | − | − |
| 19 | 78 | − | − |
| 20 | 92 | − | − |
| 27 | 94 | − | − |
| 31 | 89 | − | − |
| 32 | 87 | − | − |

TABLE 29

| Compound No. | Protective value (%) | Foliage die back | Growth retardation of plants |
|---|---|---|---|
| 33 | 71 | − | − |
| 40 | 84 | − | − |
| 42 | 87 | − | − |
| 47 | 98 | − | − |
| 49 | 94 | − | − |
| 51 | 91 | − | − |
| 55 | 91 | − | − |
| 57 | 80 | − | − |
| 60 | 82 | − | − |
| 61 | 88 | − | − |
| 65 | 96 | − | − |

TABLE 30

| Compound No. | Protective value (%) | Foliage die back | Growth retardation of plants |
|---|---|---|---|
| 66 | 95 | − | − |
| 80 | 91 | − | − |
| 90 | 74 | − | − |

TABLE 30-continued

| Compound No. | Protective value (%) | Foliage die back | Growth retardation of plants |
|---|---|---|---|
| 97 | 98 | – | – |
| 98 | 89 | – | – |
| Propenazole | 75 | – | – |
| 2,6-Dichloroiso-nicotinic acid | 85 | + | + |

Test Example 2

Test for Control of Bacterial Spot of Cucumber

Chemical solutions having an active ingredient concentration of 200 ppm prepared by diluting each wettable powder described in "Formulation Example 2" in water were applied to cucumber plants (cultivar: Tokiwa-shin-jibai) in the four-leaf stage planted in pots (diameter: 10 cm; height: 9 cm) by way of foliage application. Seven days later, a suspension of pathogenic bacteria were sprayed for inoculation later. After the cucumber plants were left in a moist chamber at 25° C. for 48 hours, they were placed in a greenhouse. The number of lesions on the lowest four leaves were investigated 7 days after the inoculation. Protective values were calculated in the same manner described in the Test Example 1. As a result, the compounds indicated as Compounds Nos. 1 to 99 showed protective values between 75 to 100%.

Tests were also conducted in a similar manner using, as a control, 2-chloro-6-hydroxyisonicotinic acid, which resulted in a protective value of 60%.

INDUSTRIAL APPLICABILITY

The present invention provides novel 2,6-dichloro-4-pyridinemethanol derivatives, agricultural chemicals containing these compounds as active ingredients, and agricultural chemicals containing 2,6-dichloro-4-pyridinemethanol and/or a benzoic acid ester thereof as an active ingredient. In particular, the present invention can provide agents for controlling plant diseases, particularly agents for controlling rice blast, with which there is little possibility of phytotoxicity for the plants, and which are sufficiently effective.

What is claimed is:

1. An agricultural agent comprising as an active ingredient at least one 2,6-dichloro-4-pyridinemethanol compound expressed by the following formula (1):

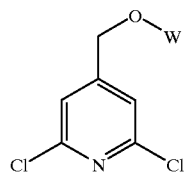

(1)

wherein W denotes: a hydrogen atom, a $C_1$ to $C_8$ alkyl group which is unsubstituted or which is optionally substituted with an alkoxy group, an alkylthio group, a cyano group, a phenyl group, or a pyridyl group, the pyridyl group being optionally substituted with a halogen atom; a trifluoromethylpyridyl group; —$COR^1$; —$SO_2R^2$; —$PO(OR^3)_2$; $CONHR^4$; —$COOR^4$; —$COCOR^4$; or —$SiR^5R^6R^7$;

$R^1$ denotes:
a $C_1$ to $C_{18}$ alkyl group which is unsubstituted or which is optionally substituted with an alkoxy group, an alkylthio group, a phenyl group, a hydroxy group, a phenylalkoxy group, a phenylalkylthio group, an alkyloxycarbonyl group, an alkylcarbonylamino group, or a phenoxy group, the phenyl group being optionally substituted with an alkoxy group;

a $C_1$ to $C_8$ alkenyl group which is optionally substituted with a phenyl group, the phenyl group being optionally substituted with an alkoxy group;

a phenyl group which is unsubstituted, or which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; phenyl group; and a phenoxy group; or a 5- or 6-membered heterocyclic ring residue which has any one of a nitrogen atom, an oxygen atom, or a sulfur atom as a ring component atom, the heterocyclic ring residue being optionally substituted with a $C_1$ to $C_4$ alkyl group;

$R^2$ denotes a $C_1$ to $C_{12}$ alkyl group or a phenyl group which is optionally substituted with a $C_1$ to $C_{12}$ alkyl group;

$R^3$ denotes a $C_1$ to $C_4$ alkyl group;

$R^4$ denotes a $C_1$ to $C_3$ alkyl group or a phenyl group; and each of $R^5$ to $R^7$, being the same or different, denotes a $C_1$ to $C_4$ alkyl group.

2. An agricultural agent comprising as an active ingredient at least one 2,6-dichloro-4-pyridinemethanol compound according to claim 1, wherein W in formula (1) denotes a $C_1$ to $C_8$ alkyl group or a trifluoromethylpyridyl group, the $C_1$ to $C_8$ alkyl group being unsubstituted or being substituted with an alkoxy group, an alkylthio group, a cyano group, a phenyl group, or a pyridyl group, the pyridyl group being optionally substituted with a halogen atom.

3. An agricultural agent comprising as an active ingredient at least one 2,6-dichloro-4-pyridinemethanol compound according to claim 1, wherein W in formula (1) denotes —$COR^1$ in which $R^1$ denotes:

a $C_1$ to $C_{18}$ alkyl group which is unsubstituted or which is substituted with an alkoxy group, an alkylthio group, phenyl group, a hydroxy group, a phenylalkoxy group, a phenylalkythio group, an alkyloxycarbonyl group, an alkylcarbonylamino group, or a phenoxy group, the phenyl group being optionally substituted with an alkoxy group;

a $C_1$ to $C_{18}$ alkenyl group which is unsubstituted or which is substituted with a phenyl group which is optionally substituted with an alkoxy group;

a phenyl group which has one or more substituent groups, being the same or different, the substituent groups being selected from: halogen atoms; $C_1$ to $C_6$ alkyl groups which are optionally substituted with a halogen atom, $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group; or a 5- or 6-membered heterocyclic ring residue which has any one of a nitrogen atom, an oxygen atom, or a sulfur atom as a ring component atom, the heterocyclic ring residue being optionally substituted with a $C_1$ to $C_4$ alkyl group.

4. An agricultural agent comprising as an active ingredient at least one 2,6- dichloro-4-pyridinemethanol compound according to claim 3, wherein W in formula (1) denotes —$COR^1$ in which $R^1$ denotes an alkenyl group which is unsubstituted or which is substituted with a phenyl group which is optionally substituted with an alkoxy group.

5. An agricultural agent comprising as an active ingredient at least one 2,6-dichloro-4-pyridinemethanol compound according to claim 3, wherein W in formula (1) denotes —$COR^1$ in which $R^1$ denotes a phenyl group which has one or more substituent groups, being the same or different, the substituent groups being selected from: halogen atoms; $C_1$ to $C_6$ alkyl groups which are optionally substituted with a halogen atom; $C_1$ to $C_{12}$ alkoxy groups which are optionally substituted with a halogen atom; $C_2$ to $C_3$ alkenyloxy groups; a nitro group; an amino group; $C_1$ to $C_4$ alkylamino groups; a cyano group; an acetylamino group; a benzoylamino group; an acetyloxy group; a phenyl group; and a phenoxy group.

6. An agricultural agent comprising as an active ingredient at least one 2,6-dichloro-4-pyridinemethanol compound according to claim 5, wherein W in formula (1) denotes —$COR^1$ in which $R^1$ denotes a $C_1$ to $C_{12}$ alkoxyphenyl group which is optionally substituted with a halogen atom.

7. An agricultural agent comprising as an active ingredient at least one 2,6-dichloro-4-pyridinemethanol compound according to claim 1, wherein W in formula (1) denotes —$SO_2R^2$ in which $R^2$ denotes a $C_1$ to $C_{12}$ alkyl group or phenyl group which is optionally substituted with a $C_1$ to $C_{12}$ alkyl group.

8. An agricultural agent comprising as an active ingredient at least one 2,6-dichloro-4-pyridinemethanol compound according to claim 1, wherein W in formula (1) denotes —$PO(OR^3)_2$ in which $R^3$ denotes a $C_1$ to $C_4$ alkyl group.

9. An agriculturall agent comprising as an active ingredient at least one 2,6-dichloro-4-pyridinemethanol compound according to claim 1, wherein W in formula (1) denotes —$CONHR^4$, —$COOR^4$, or —$COCOR^4$, in which $R^4$ denotes a $C_1$ to $C_3$ alkyl group or a phenyl group.

10. An agricultural agent comprising as an active ingredient at least one 2,6-dichloro-4-pyridinemethanol compound according to claim 1, wherein W in formula (1) denotes —$SiR^5R^6R^7$ in which each of $R^5$ to $R^7$, being the same or different, denotes a $C_1$ to $C_4$ alkyl group.

11. An agricultural agent according to claim 1, wherein the agricultural agent is an agent for controlling a plant disease.

12. An agricultural agent according to claim 11, wherein the agent for controlling a plant disease is an agent for controlling rice blast.

* * * * *